United States Patent
McMackin et al.

(10) Patent No.: US 7,019,835 B2
(45) Date of Patent: Mar. 28, 2006

(54) METHOD AND SYSTEM TO MEASURE CHARACTERISTICS OF A FILM DISPOSED ON A SUBSTRATE

(75) Inventors: Ian M. McMackin, Austin, TX (US); Phillip D. Schumaker, Austin, TX (US); Byung-Jin Choi, Austin, TX (US); Sidlgata V. Sreenivasan, Austin, TX (US); Michael P. C. Watts, Austin, TX (US)

(73) Assignee: Molecular Imprints, Inc., Austin, TX (US)

( * ) Notice: Subject to any disclaimer, the term of this patent is extended or adjusted under 35 U.S.C. 154(b) by 99 days.

(21) Appl. No.: 10/782,187

(22) Filed: Feb. 19, 2004

(65) Prior Publication Data

US 2005/0185169 A1 Aug. 25, 2005

(51) Int. Cl.
*G01B 11/00* (2006.01)
*G03F 1/00* (2006.01)

(52) U.S. Cl. .................. 356/394; 356/237.5; 340/5; 340/30

(58) Field of Classification Search .. 356/237.1–237.6, 356/394; 430/5, 30, 17, 22, 312, 316, 394, 430/393
See application file for complete search history.

(56) References Cited

U.S. PATENT DOCUMENTS

| | | | |
|---|---|---|---|
| 4,444,801 A * | 4/1984 | Hongo et al. .................. 427/10 |
| 4,512,848 A | 4/1985 | Deckman et al. |
| 4,722,878 A | 2/1988 | Watakabe et al. |
| 4,731,155 A | 3/1988 | Napoli et al. |
| 5,028,366 A | 7/1991 | Harakal et al. |
| 5,235,400 A * | 8/1993 | Terasawa et al. ........ 356/237.5 |
| 5,331,407 A * | 7/1994 | Doi et al. .................... 356/394 |
| 5,425,848 A | 6/1995 | Haisma et al. |
| 5,563,702 A | 10/1996 | Emery et al. |
| 5,601,641 A | 2/1997 | Stephens |
| 5,625,193 A | 4/1997 | Broude et al. |
| 5,669,303 A | 9/1997 | Maracas et al. |
| 5,772,905 A | 6/1998 | Chou |
| 5,774,574 A * | 6/1998 | Hoki ........................... 382/149 |
| 5,837,892 A | 11/1998 | Cavallaro et al. |
| 5,849,209 A | 12/1998 | Kindt-Larsen et al. |
| 5,849,222 A | 12/1998 | Jen et al. |
| 6,016,696 A | 1/2000 | Bair et al. |

(Continued)

FOREIGN PATENT DOCUMENTS

JP 02-24848 1/1990

(Continued)

OTHER PUBLICATIONS

U.S. Appl. No. 10/996,126, filed Nov. 23, 2004, Sreenivasan et al.

(Continued)

*Primary Examiner*—Gregory J. Toatley, Jr.
*Assistant Examiner*—Sang H. Nguyen
(74) *Attorney, Agent, or Firm*—Michael D. Carter

(57) ABSTRACT

The present invention is directed to providing a method and system to measure characteristics of a film disposed on a substrate. The method includes identifying a plurality of processing regions on the film; measuring characteristics of a subset of the plurality of processing regions, defining measured characteristics; determining a variation of one of the measured characteristics; and associating a cause of the variations based upon a comparison of the one of the measured characteristics to measured characteristics associated with the remaining processing regions of the subset. The system carries out the aforementioned method.

28 Claims, 9 Drawing Sheets

U.S. PATENT DOCUMENTS

| | | | |
|---|---|---|---|
| 6,052,183 A | 4/2000 | Lee | |
| 6,112,588 A | 9/2000 | Cavallaro et al. | |
| 6,133,576 A | 10/2000 | Shafer et al. | |
| 6,245,581 B1 | 6/2001 | Bonser et al. | |
| 6,278,519 B1 | 8/2001 | Rosencwaig et al. | |
| 6,297,880 B1 | 10/2001 | Rosencwaig et al. | |
| 6,309,580 B1 | 10/2001 | Chou | |
| 6,334,960 B1 * | 1/2002 | Willson et al. | 216/52 |
| 6,387,787 B1 | 5/2002 | Mancini et al. | |
| 6,391,217 B1 | 5/2002 | Schaffer et al. | |
| 6,482,742 B1 | 11/2002 | Chou | |
| 6,517,995 B1 | 2/2003 | Jacobson et al. | |
| 6,518,189 B1 | 2/2003 | Chou | |
| 6,561,706 B1 | 5/2003 | Singh et al. | |
| 6,580,172 B1 | 6/2003 | Mancini et al. | |
| 6,603,538 B1 | 8/2003 | Oluseyi et al. | |
| 6,633,391 B1 | 10/2003 | Oluseyi et al. | |
| 6,646,662 B1 | 11/2003 | Nebashi et al. | |
| 6,696,220 B1 | 2/2004 | Bailey et al. | |
| 6,713,238 B1 | 3/2004 | Chou et al. | |
| 6,746,319 B1 * | 6/2004 | Tada et al. | 451/285 |
| 6,771,374 B1 * | 8/2004 | Rangarajan et al. | 356/445 |
| 6,776,094 B1 | 8/2004 | Whitesides et al. | |
| 6,809,356 B1 | 10/2004 | Chou | |
| 6,828,244 B1 | 12/2004 | Chou | |
| 6,871,558 B1 | 3/2005 | Choi et al. | |
| 6,900,881 B1 | 5/2005 | Sreenivasan et al. | |
| 6,908,861 B1 | 6/2005 | Sreenivasan et al. | |
| 6,916,584 B1 | 7/2005 | Sreenivasan et al. | |
| 2002/0042027 A1 | 4/2002 | Chou et al. | |
| 2002/0132482 A1 | 9/2002 | Chou | |
| 2002/0167117 A1 | 11/2002 | Chou | |
| 2002/0177319 A1 | 11/2002 | Chou | |
| 2003/0034329 A1 | 2/2003 | Chou | |
| 2003/0080471 A1 | 5/2003 | Chou | |
| 2003/0080472 A1 | 5/2003 | Chou | |
| 2003/0205658 A1 | 11/2003 | Voisin | |
| 2004/0007799 A1 | 1/2004 | Choi et al. | |
| 2004/0008334 A1 | 1/2004 | Sreenivasan et al. | |
| 2004/0009673 A1 | 1/2004 | Sreenivasan et al. | |
| 2004/0021254 A1 | 2/2004 | Sreenivasan et al. | |
| 2004/0021866 A1 | 2/2004 | Watts et al. | |
| 2004/0022888 A1 | 2/2004 | Sreenivasan et al. | |
| 2004/0036201 A1 | 2/2004 | Chou et al. | |
| 2004/0046288 A1 | 3/2004 | Chou | |
| 2004/0110856 A1 | 6/2004 | Young et al. | |
| 2004/0112153 A1 | 6/2004 | Choi et al. | |
| 2004/0118809 A1 | 6/2004 | Chou et al. | |
| 2004/0124566 A1 | 7/2004 | Sreenivasan et al. | |
| 2004/0131718 A1 | 7/2004 | Chou et al. | |
| 2004/0137734 A1 | 7/2004 | Chou et al. | |
| 2004/0156108 A1 | 8/2004 | Chou et al. | |
| 2004/0192041 A1 | 9/2004 | Jeong et al. | |
| 2004/0197843 A1 | 10/2004 | Chou et al. | |
| 2004/0223883 A1 | 11/2004 | Choi et al. | |
| 2004/0250945 A1 | 12/2004 | Zheng et al. | |
| 2005/0028618 A1 | 2/2005 | Choi et al. | |
| 2005/0037143 A1 | 2/2005 | Chou et al. | |

FOREIGN PATENT DOCUMENTS

| | | |
|---|---|---|
| JP | 02-92603 | 4/1990 |
| WO | WO 99/05724 | 2/1999 |
| WO | WO 00/21689 | 4/2000 |
| WO | WO 01/47003 | 6/2001 |
| WO | WO 02/07199 | 1/2002 |
| WO | WO 03/010289 | 2/2003 |
| WO | WO 03/079416 | 9/2003 |
| WO | WO 03/099536 | 12/2003 |
| WO | WO 2004/114016 | 12/2004 |

OTHER PUBLICATIONS

Chou, Nanoimprint Lithography and Lithographically Induced Self-Assembly, MRS Bulletin, pp. 512-517, Jul. 1, 2001.

Choi et al., Design of Orientation Stages for Step and Flash Imprint Lithography, Precision Engineering, pp. 192-199, Jan. 1, 2001.

Colburn et al., Step and Flash Imprint Lithography for sub-100 nm Patterning, Proceedings of SPIE vol. 3997 pp. 453-457, Jan. 1, 2000.

Chou et al., Imprint Lithography with 25-Nanometer Resolution, Science vol. 272, pp. 85-87, Apr. 5, 1996.

Chou et al., Imprint Lithography with Sub-10 nm Feature Size and High Throughput, Microelectronic Engineering 35, pp. 237-240, Jan. 1, 1997.

Haisma et al., Mold-assisted Nanolithography: A Process for Reliable Pattern Replication, J. Vac. Sci. Technol. B, pp 4124-4128, Nov. 1, 1996.

Chou et al., Imprint of Sub-25 nm Vias and Trenches in Polymers, Appl. Phys. Lett. 67 (21), Nov. 20, 1995.

Johnson et al., Advances in Step and Flash Imprint Lithography, SPIE Microlithography Conference, Feb. 23, 2003.

Chou et al., Lithographically Induced Self-assembly of Periodic Polymer Micropillar Arrays, J. Vac. Sci. Technol. B 17 (6), pp. 3197-3202, Nov. 1, 1999.

Colburn et al., Step and Flash Imprint Lithography: A New Approach to High-Resolution Patterning, Proc. Of SPIE, vol. 3676, Mar. 1, 1999.

Heidari, Nanoimprint Lithography at the 6 in. Wafer Scale, J. Vac. Sci. Technol. B 18(6), pp. 3557-3560, Nov. 1, 2000.

Translation of Japanese Patent 02-92603.

Translation of Japanese Patent 02-24848.

Chou et al., Ultrafast and Direct Imprint of Nanostructures in Silicon, Nature, Col. 417, (Jun. 2002), pp. 835-837, Jun. 1, 2002.

Chou et al., Nanoimprint Lithography, Journal of Vacuum Science Technology B 14(16), pp. 4129-4133, Nov. 1, 1996.

Colburn et al., Development and Advantages of Step-and-Flash Lithography, Solid State Technology, Jul. 1, 2001.

Colburn et al., Characterization and Modeling of Volumetric and Mechnical Properties for Step and Flash Imprint Lithography Photopolymers, Journal of Vacuum Science Technology. vol. b. 19(6), Nov. 1, 2001.

Bailey et al., Step and Flash Imprint Lithography: Defect Analysis, Journal of Vacuum Science, B 19(6), pp. 2806-2810, Nov. 1, 2001.

Bailey et al., Step and Flash Imprint Lithography: Template Surface Treatment and Defect Analysis, Journal of Vacuum Science, B 18(6), pp. 3572-3577, Nov. 1, 2000.

Schneider et al., Stripes of Partially Fluorinated Alkyl Chains: Dipolar Langmuir Monolayers.

U.S. Appl. No. 11/126,946, naming Inventors Choi et al., entitled Formation of Discontinuous Films During an Imprint Lithography Process, filed May 11, 2005.

U.S. Appl. No. 11/127,041, naming Inventors Sreenivasan et al., entitled Step and Repeat Imprint Lithography Processes, filed May 11, 2005.

U.S. Appl. No. 11/127,060, naming Inventors Sreenivasan et al., entitled Step and Repeat Imprint Lithography Systems, filed May 11, 2005.

* cited by examiner

1

METHOD AND SYSTEM TO MEASURE CHARACTERISTICS OF A FILM DISPOSED ON A SUBSTRATE

BACKGROUND OF THE INVENTION

The field of invention relates generally to imprint lithography. More particularly, the present invention is directed measuring characteristics of a films patterned employing imprint lithography processes.

Micro-fabrication involves the fabrication of very small structures, e.g., having features on the order of micro-meters or smaller. One area in which micro-fabrication has had a sizeable impact is in the processing of integrated circuits. As the semiconductor processing industry continues to strive for larger production yields while increasing the circuits per unit area formed on a substrate, micro-fabrication becomes increasingly important. Micro-fabrication provides greater process control while allowing increased reduction of the minimum feature dimension of the structures formed. Other areas of development in which micro-fabrication has been employed include biotechnology, optical technology, mechanical systems and the like.

Exemplary micro-fabrication technique are disclosed in U.S. Pat. No. 6,334,960 to Willson et al. and by Chou et al. in *Ultrafast and Direct Imprint of Nanostructures in Silicon, Nature*, Col. 417, pp. 835–837, June 2002, which is referred to as a laser assisted direct imprinting (LADI) process. Both of these processes involve the use of forming a layer on a substrate by embossing a flowable material with a mold and subsequently solidifying the flowable material to form a patterned layer.

As a result of the small size of the features produced by micro-fabrication techniques, process diagnostics become increasingly important to determine the characteristics of films during processing and after processing. Many prior art process control and diagnostic techniques to facilitate determination of film characteristics have been employed in standard semiconductor processing operations. However, many of the existing process control and diagnostic techniques are not suitable for use with the embossing technique employed during micro-fabrication.

Thus, a need exists for providing improved process and diagnostic techniques for use with micro-fabrication processes, such as imprint lithography.

SUMMARY OF THE INVENTION

The present invention is directed to providing a method and system to measure characteristics of a film disposed on a substrate. The method includes identifying a plurality of processing regions on the film; measuring characteristics of a subset of the plurality of processing regions, defining measured characteristics; determining a variation of one of the measured characteristics; and associating a cause of the variations based upon a comparison of the one of the measured characteristics to measured characteristics associated with the remaining processing regions of the subset. The system carries out the aforementioned method. These and other embodiments are discussed more fully below.

DETAILED DESCRIPTION OF THE INVENTION

Figure 1:
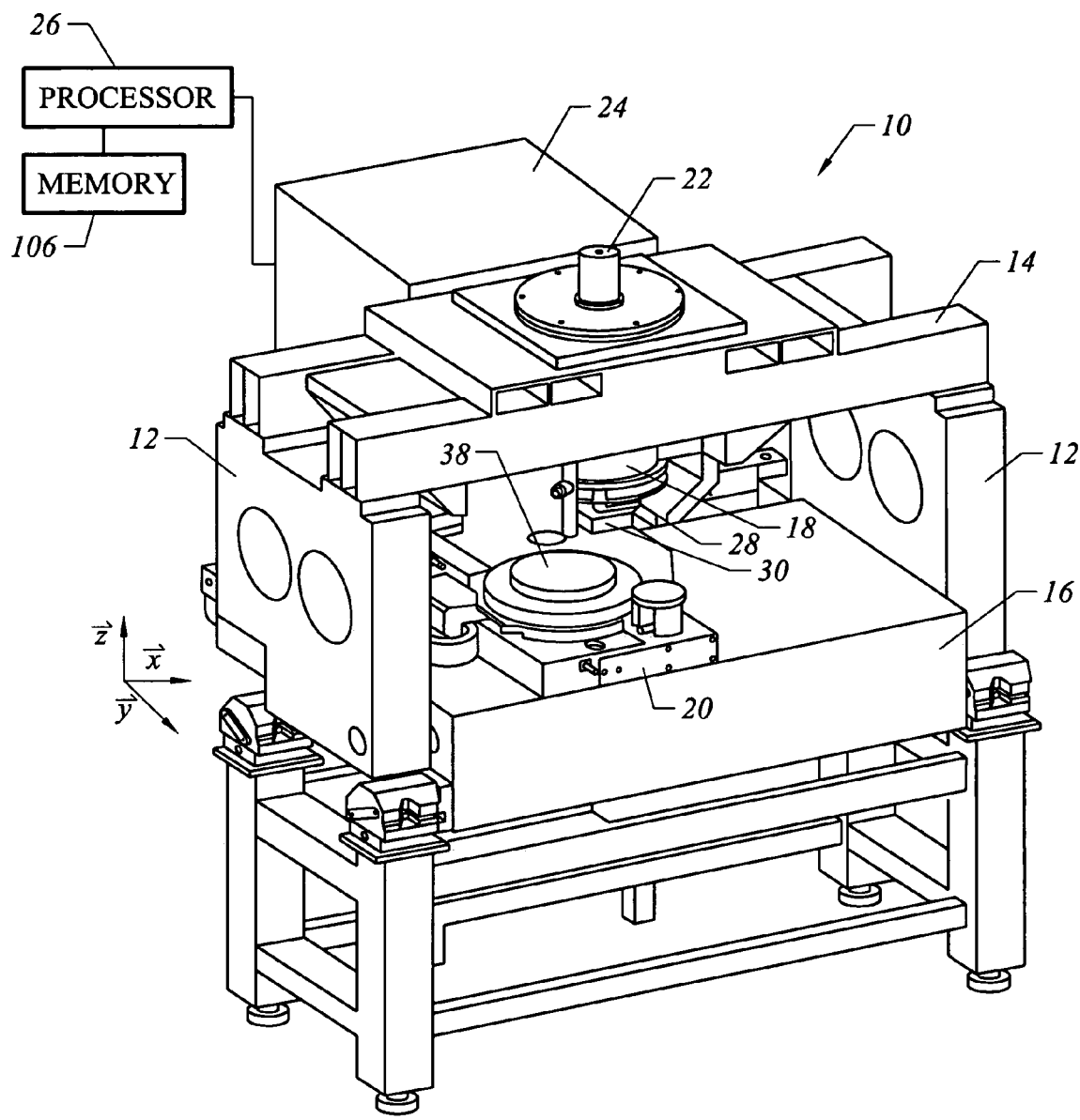
FIG. 1 is a perspective view of a lithographic system in accordance with the present invention.

FIG. 1 depicts a lithographic system 10 in accordance with one embodiment of the present invention that includes a pair of spaced-apart bridge supports 12 having a bridge 14 and a stage support 16 extending therebetween. Bridge 14 and stage support 16 are spaced-apart. Coupled to bridge 14 is an imprint head 18, which extends from bridge 14 toward stage support 16 and provides movement along the Z-axis. Disposed upon stage support 16 to face imprint head 18 is a motion stage, referred to as a substrate support stack 20. Substrate support stack 20 is configured to move with respect to stage support 16 along X- and Y-axes. It should be understood that imprint head 18 may provide movement along the X- and Y-axes, as well as the Z-axis, and motion stage 20 may provide movement in the Z-axis, as well as the X- and Y-axes. An exemplary substrate support stack 20 is disclosed in U.S. patent application Ser. No. 10/194,414, filed Jul. 11, 2002, entitled "Step and Repeat Imprint Lithography Systems," assigned to the assignee of the present invention, and which is incorporated by reference herein in its entirety. A radiation source 22 is coupled to lithographic system 10 to impinge actinic radiation upon substrate support stack 20. As shown, radiation source 22 is coupled to bridge 14 and includes a power generator 24 connected to radiation source 22. Operation of lithographic system 10 is typically controlled by a processor 26 that is in data communication therewith.

Figure 2:
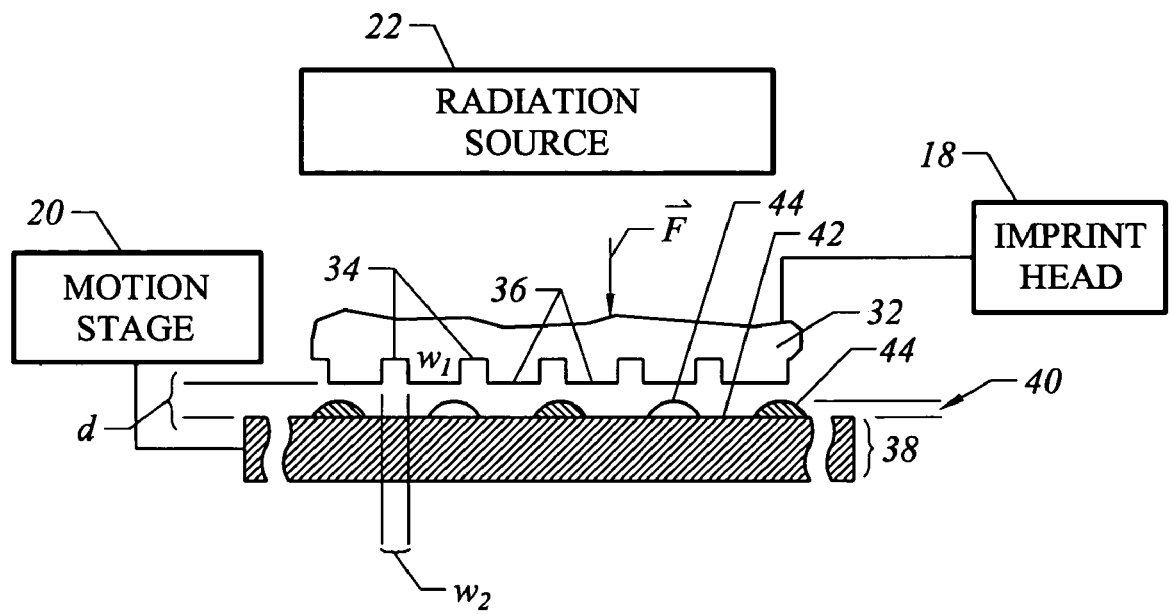
FIG. 2 is a simplified elevation view of a lithographic system shown in FIG. 1.

Referring to both FIGS. 1 and 2, included in imprint head 18, is a chuck 28 to which a template 30 having a mold 32 thereon is mounted. An imprint head 18 and chuck 28 is disclosed in U.S. patent application Ser. No. 10/293,224, entitled "A Chucking System for Modulating Shapes of Substrates" filed Nov. 13, 2002, which is assigned to the assignee of the present invention and incorporated by reference herein, as well as U.S. patent application Ser. No. 10/316,963, entitled "A Method for Modulating Shapes of Substrates" filed Dec. 11, 2002, which is assigned to the assignee of the present invention and incorporated by reference herein. Mold 32 includes a plurality of features defined by a plurality of spaced-apart recessions 34 and protrusions 36. The plurality of features defines an original pattern that forms the basis of a pattern that is to be transferred into a wafer 38 positioned on motion stage 20. To that end, imprint head 18 and/or motion stage 20 may vary a distance "d" between mold 32 and wafer 38. In this manner, the features on mold 32 may be imprinted into a flowable region of wafer 38, discussed more fully below. Radiation source 22 is located so that mold 32 is positioned between radiation source 22 and wafer 38. As a result, mold 32 is fabricated from a material that allows it to be substantially transparent to the radiation produced by radiation source 22.

Figure 3:
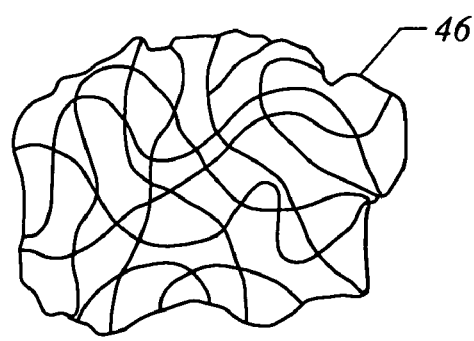
FIG. 3 is a simplified representation of material from which an imprinting layer, shown in FIG. 2, is comprised before being polymerized and cross-linked.

Referring to both FIGS. 2 and 3, a flowable region, such as an imprinting layer 40, is disposed on a portion of a surface 42 that presents a substantially planar profile. A flowable region may be formed using any known technique, such as a hot embossing process disclosed in U.S. Pat. No. 5,772,905, which is incorporated by reference in its entirety herein, or a laser assisted direct imprinting (LADI) process of the type described by Chou et al. in *Ultrafast and Direct Imprint of Nanostructures in Silicon, Nature*, Col. 417, pp. 835–837, June 2002. In the present embodiment, however, a flowable region consists of imprinting layer 40 being deposited as a plurality of spaced-apart discrete beads 44 of a material 46 on wafer 38, discussed more fully below. An exemplary system for depositing beads 44 is disclosed in U.S. patent application Ser. No. 10/191,749, filed Jul. 9, 2002, entitled "System and Method for Dispensing Liquids," and which is assigned to the assignee of the present invention, and which is incorporated by reference in its entirety herein. Imprinting layer 40 is formed from material 46 that may be selectively polymerized and cross-linked to record the original pattern therein, defining a recorded pattern. An exemplary composition for material 46 is disclosed in U.S. patent application Ser. No. 10/463,396, filed Jun. 16, 2003 and entitled "Method to Reduce Adhesion Between a Conformable Region and a Pattern of a Mold," which is incorporated by reference in its entirety herein. Material 46 is shown in FIG. 4 as being cross-linked at points 48, forming a cross-linked polymer material 50.

Figure 5:
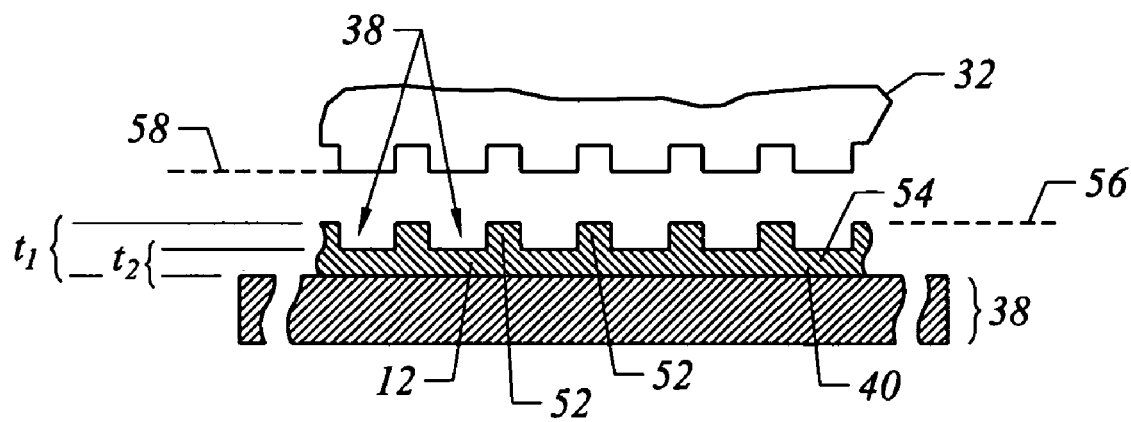
FIG. 5 is a simplified elevation view of a mold spaced-apart from the imprinting layer, shown in FIG. 1, after patterning of the imprinting layer.

Referring to FIGS. 2, 3 and 5, the pattern recorded in imprinting layer 40 is produced, in part, by mechanical contact with mold 32. To that end, distance "d" is reduced to allow imprinting beads 44 to come into mechanical contact with mold 32, spreading beads 44 so as to form imprinting layer 40 with a contiguous formation of material 46 over surface 42. In one embodiment, distance "d" is reduced to allow sub-portions 52 of imprinting layer 40 to ingress into and fill recessions 34.

To facilitate filling of recessions 34, material 46 is provided with the requisite properties to completely fill recessions 34, while covering surface 42 with a contiguous formation of material 46. In the present embodiment, sub-portions 54 of imprinting layer 40 in superimposition with protrusions 36 remain after the desired, usually minimum, distance "d", has been reached, leaving sub-portions 52 with a thickness $t_1$, and sub-portions 54 with a thickness $t_2$. Thicknesses "$t_1$" and "$t_2$" may be any thickness desired, dependent upon the application.

Figure 4:
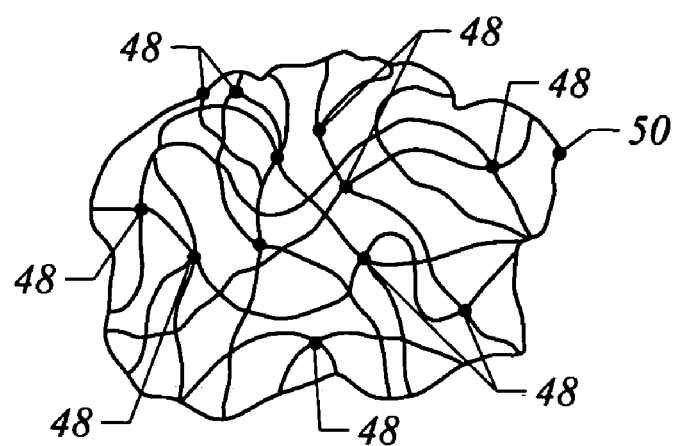
FIG. 4 is a simplified representation of cross-linked polymer material into which the material shown in FIG. 3 is transformed after being subjected to radiation.

Referring to FIGS. 2, 3 and 4, after a desired distance "d" has been reached, radiation source 22 produces actinic radiation that polymerizes and cross-links material 46, forming cross-linked polymer material 50. As a result, the composition of imprinting layer 40 transforms from material 46 to cross-linked polymer material 50, which is a solid. Specifically, cross-linked polymer material 50 is solidified to provide side 56 of imprinting layer 40 with a shape conforming to a shape of a surface 58 of mold 32, shown more clearly in FIG. 5. After imprinting layer 40 is transformed to consist of cross-linked polymer material 50, shown in FIG. 4, imprint head 18, shown in FIG. 2, is moved to increase distance "d" so that mold 32 and imprinting layer 40 are spaced-apart.

Figure 6:
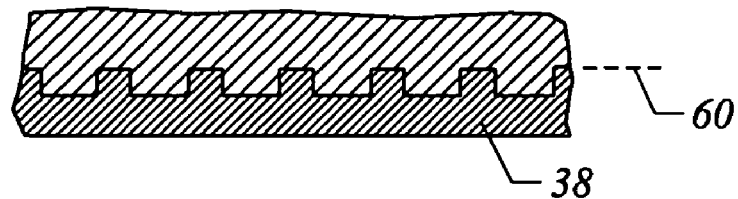
FIG. 6 is a simplified elevation view of an additional imprinting layer positioned atop of the substrate, shown in FIG. 5, after the pattern in the first imprinting layer is transferred therein.

Referring to FIG. 5, additional processing may be employed to complete the patterning of wafer 38. For example, wafer 38 and imprinting layer 40 may be etched to transfer the pattern of imprinting layer 40 into wafer 38, providing a patterned surface 60, shown in FIG. 6. To facilitate etching, the material from which imprinting layer 40 is formed may be varied to define a relative etch rate with respect to wafer 38, as desired. The relative etch rate of imprinting layer 40 to wafer 38 may be in a range of about 1.5:1 to about 100:1.

Figure 7:
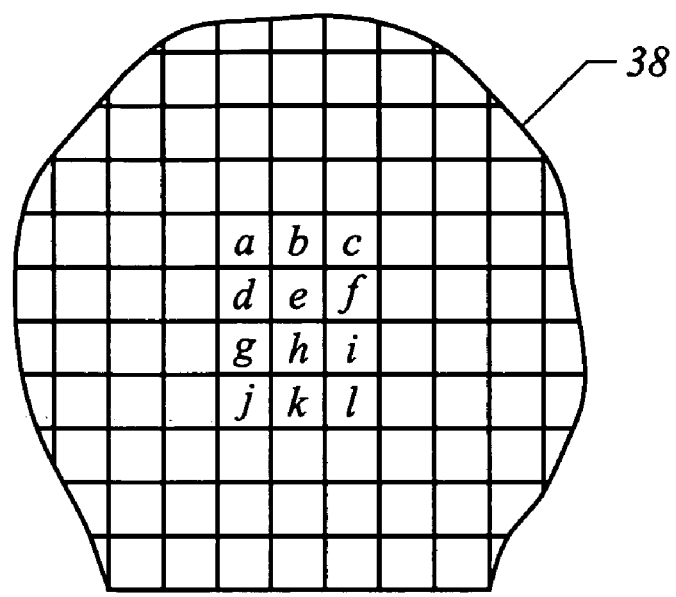
FIG. 7 is a top down view of the substrate shown in FIGS. 1 and 2.
Figure 8:
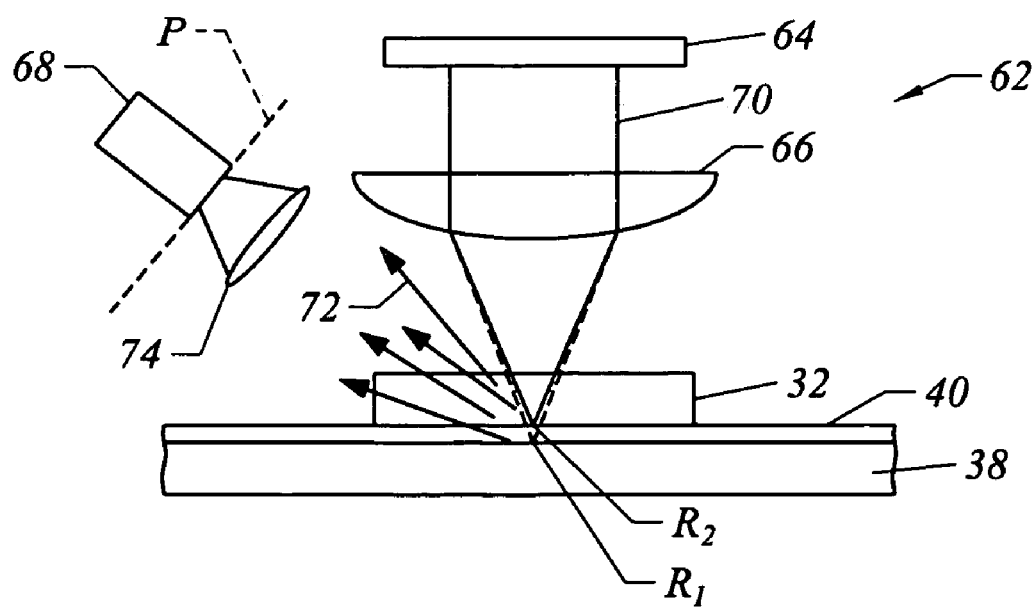
FIG. 8 is a plan view of a sensing system in accordance with the present invention.

Referring to FIGS. 7 and 8, typically the entire wafer 38 is patterned employing a step-and-repeat process. The step-and-repeat processes includes defining a plurality of regions, shown as, a–l, on wafer 38 in which the original pattern on mold 32 will be recorded. The original pattern on mold 32 may be coextensive with the entire surface of mold 32, or simply located to a sub-portion thereof. The present invention will be discussed with respect to the original pattern being coextensive with the surface of mold 32 that faces wafer 38. Proper execution of a step-and-repeat process may include proper alignment of mold 32 with each of regions a–l. To that end, mold 32 includes alignment marks (not shown). One or more of regions a–l includes fiducial marks (not shown). By ensuring that alignment marks (not shown) are properly aligned with fiducial marks (not shown), proper alignment of mold 32 with one of regions a–l in superimposition therewith is ensured. To that end, sensing device 62, discussed more fully below, may be employed. In this manner, mold 32 is sequentially contacted with each of processing regions a–l to record a pattern thereon.

Sensing device 62 may also be employed to facilitate process diagnostics. To that end, sensing device 62 includes a light source 64 and an optical train 66 to focus light upon wafer 38. Sensing device 62 is configured to focus alignment radiation reflected from regions a–l onto a single focal plane, P, wherein an optical sensor 68 may be positioned. As a result, optical train 66 may be configured to provide wavelength-dependent focal lengths, should it be desired and differing wavelengths of light employed. Light may be produced in any manner known in the art. For example, a single broadband source of light, shown as a light 70, may produce wavelengths that impinge upon optical train 66. Optical band-pass filters (not shown) may be disposed between the broadband source and the alignment marks (not shown).

Alternatively, a plurality of sources of light (not shown) may be employed, each one of which produces distinct wavelengths of light. Light 70 is focused by optical train 66 to impinge upon regions a–l at one or more regions, shown as region $R_1$ and region $R_2$. Light reflects from regions $R_1$ and $R_2$, shown as a reflected light 72, and is collected by a collector lens 74. Collector lens 74 focuses all wavelengths of reflected light 72 onto plane P so that optical sensor 68 detects reflected light 72. The reflected light contains information concerning characteristics of imprinting layer 40 using well known techniques. For example, characteristics, such as, film thickness, pattern quality, pattern alignment, pattern critical dimension variation and the like may be obtained by light sensed by sensor 68. The information sensed by sensor 68 is transmitted to processor 26 that quantizes the same to create measurement quantizations. Processor 26 may then compare information received from sensor 68 to a priori information contained in a look up table, for example in memory 106, to determine whether anomalies are present in imprinting layer 40 of regions a–l.

Referring to FIGS. 1 and 7, were an anomaly found in the pattern generated in a processing region a–l, the step-and-repeat imprinting process is found to facilitate determining a source of the anomaly. For example, were it found that a substantially similar anomaly was found in each of processing regions a–l, it could be deduced that imprint head 18 was the cause of the anomaly. To determine which subsystem of imprint head 18 contributed to, or caused, the anomaly, the subsystems could be systematically replaced.

Figure 9:
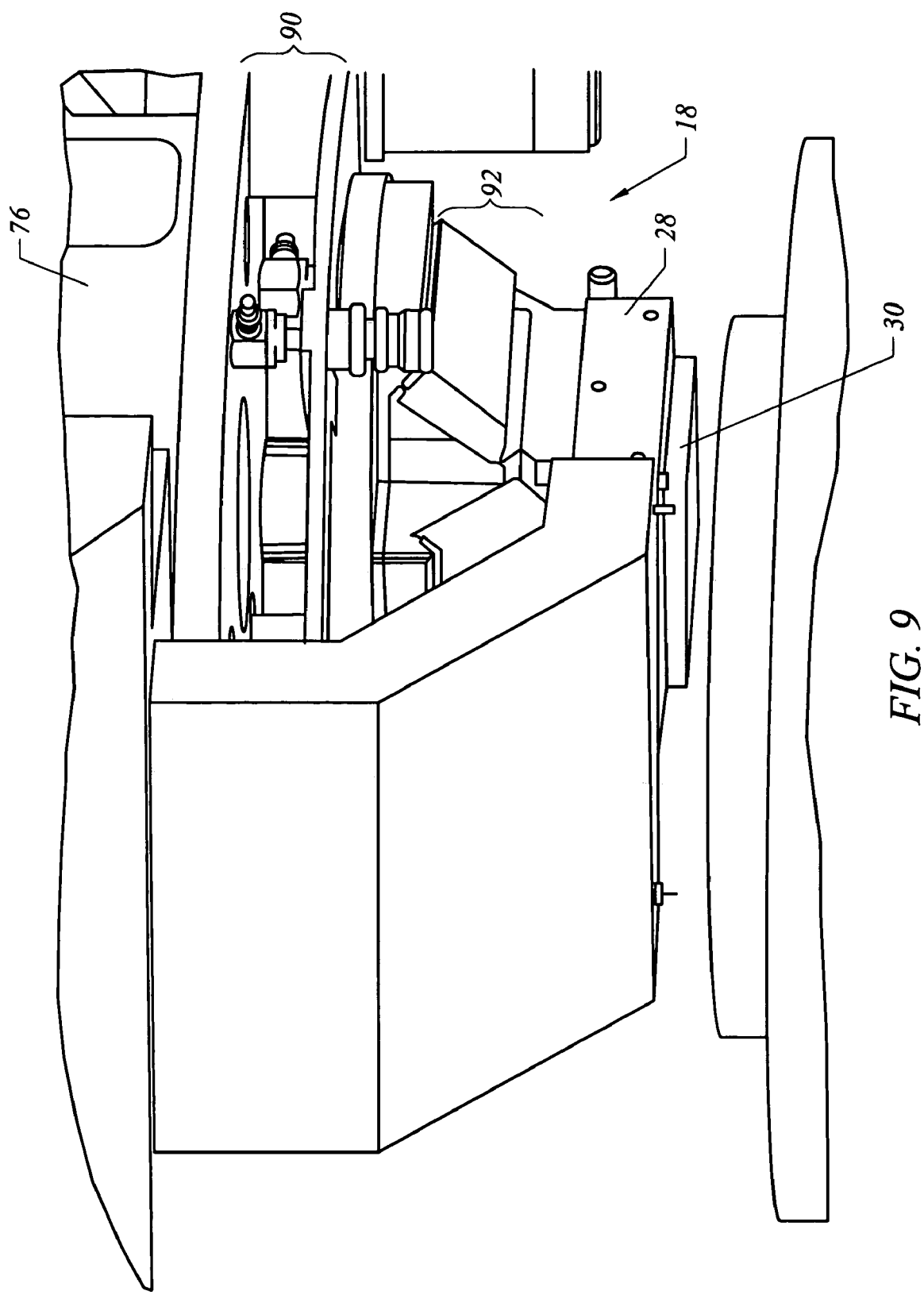
FIG. 9 is a detailed perspective view of an imprint head shown in FIG. 1.
Figure 10:
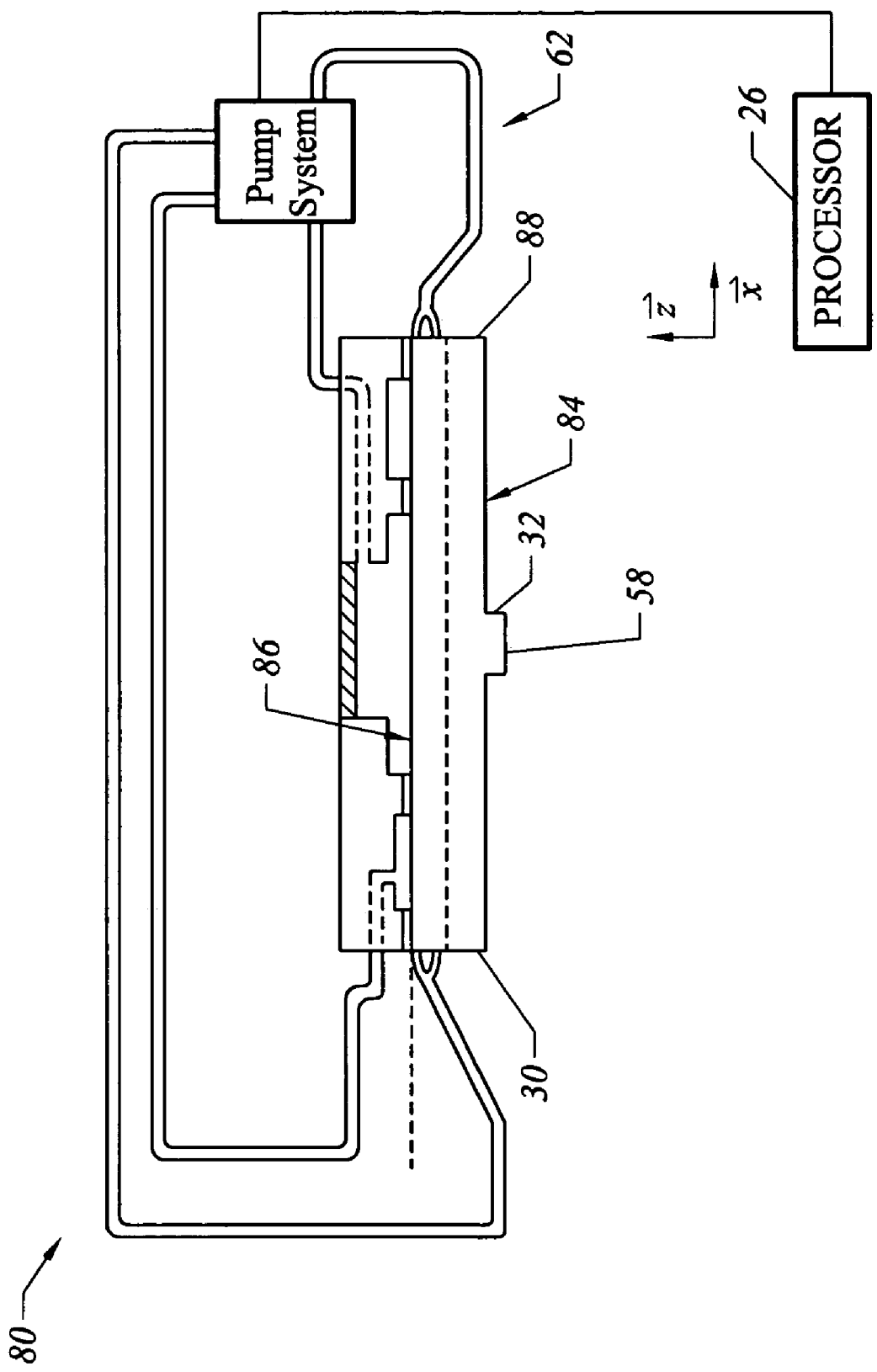
FIG. 10 is a detailed cross-sectional view of a substrate, having a mold thereon, attached to a chucking system, shown in FIG. 1.

For example, referring to FIGS. 9 and 10, imprint head 18 includes many subsystems, such as head housing 76 to which template 30 is coupled via a chucking system 80 that includes chuck body 28. Specifically, template 30 includes opposed surfaces 84 and 86 and a periphery surface 88 extending therebetween. Surface 86 faces chucking system 80, and mold 32 extends from surface 84. To ensure that fluid from beads 44, shown in FIG. 2, do not spread beyond the area of mold 32, surface 58 of mold 32 is spaced-apart from surface 84 of template 30 a distance on the order of micron, e.g., 15 microns. A calibration system 90 is coupled to imprint head housing 76, and chuck body 28 couples template 30 to calibration system 90 vis-à-vis a flexure system 92. Calibration system 90 facilitates proper orientation alignment between template 30 and wafer 38, shown in FIG. 2, thereby achieving a substantially uniform gap distance, "d", therebetween.

Figure 11:
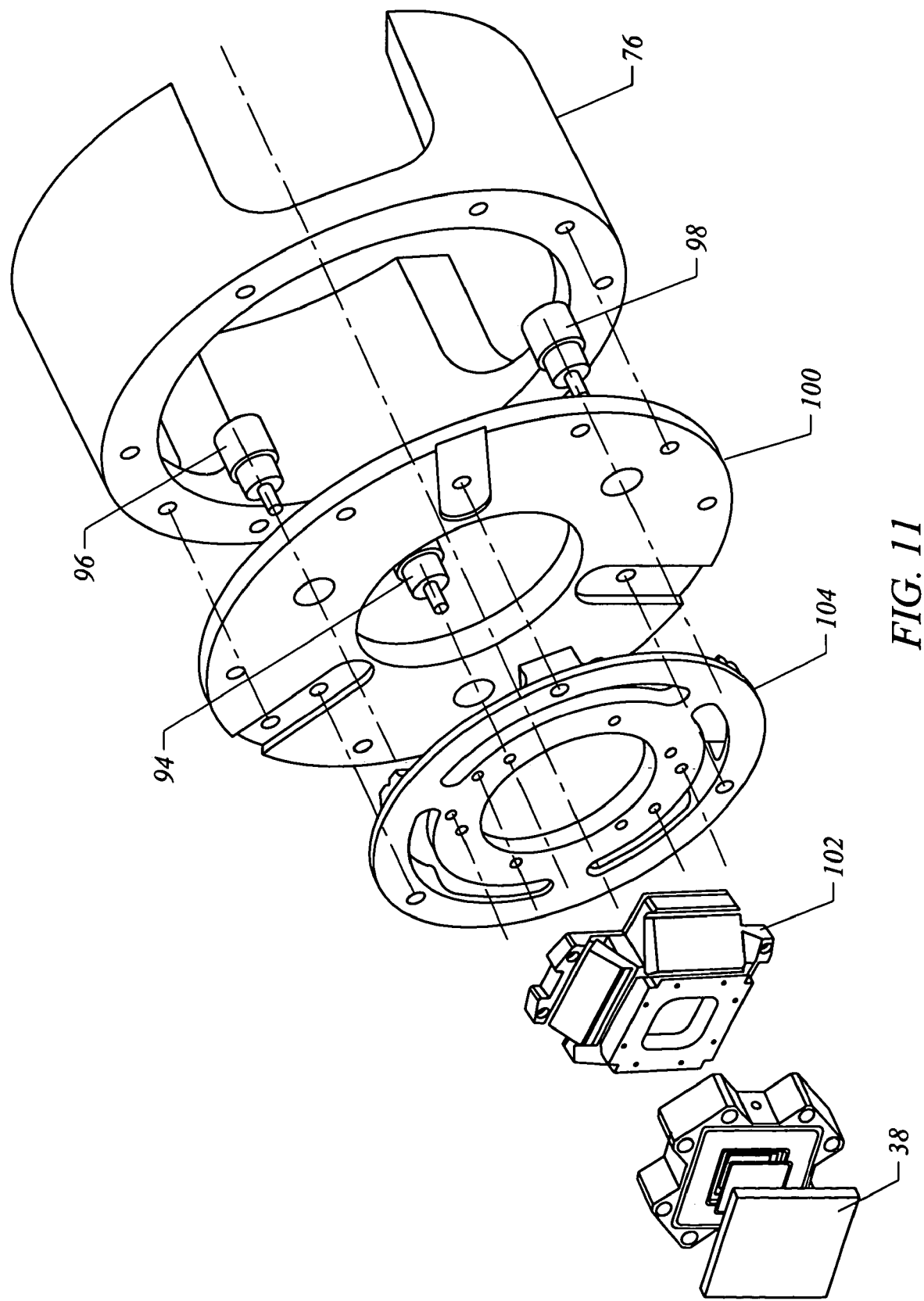
FIG. 11 is an exploded perspective view of the imprint head shown in FIG. 9.

Referring to both FIGS. 9 and 11, calibration system 90 includes a plurality of actuators 94, 96 and 98 and a base plate 100. Specifically, actuators 94, 96 and 98 are connected between housing 76 and base plate 100. Flexure system 92 includes flexure springs 102 and flexure ring 104. Flexure ring 104 is coupled between base plate 100 and flexure springs 102. Motion of actuators 94, 96 and 98 orientates flexure ring 104 that may allow for a coarse calibration of flexure springs 102 and, therefore, chuck body 28 and template 30. Actuators 94, 96 and 98 also facilitate translation of flexure ring 104 to the Z-axis. Flexure springs 102 include a plurality of linear springs that facilitate gimbal-like motion in the X-Y plane so that proper orientation alignment may be achieved between wafer 38 and template 30, shown in FIG. 2.

Referring to FIGS. 1, 10 and 11, to determine whether mold 32 attributed to an anomaly, template 30 would be replaced. Were the anomaly absent, then it could be concluded that mold 32 was the source of the anomaly. Were the anomaly still present, another subsystem of imprint head 18 could be replaced, such as, flexure springs 102. Were the anomaly found to be absent in patterns of other regions a–l, and then it could be concluded that flexure springs 102 were the source. Were the anomaly still present, the other subsystems could be replaced, such as chuck body 28, actuators 94, 96, and 98, flexure ring 104 and the like.

Were it observed that the anomaly appeared in only one of processing regions, then it could be deduced that substrate support stack 20 was the cause of the anomaly. As discussed above with respect to imprint head 18, the subsystems of substrate support stack 20 may be individually replaced to identify the subsystem attributing to the anomaly.

It should also be understood, however, that anomalies and their sources may be determined without the use of Step-and-Repeat imprinting, e.g., with whole wafer patterning techniques. To that end, batches of substrates are examined during processing to determine whether anomalies are present on successive substrates. Were it found that a substantially similar anomaly was found in the same region, or a similar anomaly in differing regions, on successive wafers 38, it could be deduced that mold 32 or chuck 28 was the cause of the defect. This could be verified by replacing mold 32. Were the anomaly still present, it could be concluded that the cause of the anomaly was chuck 28. Were the anomaly found not to repeat upon replacement of mold 32, it could be concluded that mold 32 was the cause of the anomaly. Were it observed that the anomaly appeared on a limited number or one of wafers 38, then it could be deduced that wafer 38 was the cause of the anomaly.

Figure 12:
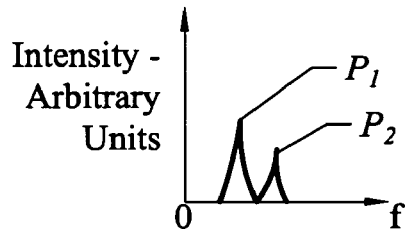
FIG. 12 is a graph showing the mapping of reflected radiation, sensed by the sensing system shown in FIG. 8, in a frequency domain in accordance with the present invention.

For example, the anomaly could be a film thickness variation. To that end, any one of a number of film thickness measurements can be employed, such as ellipsometry, scatterometry, broad-band spectrometry and the like. An exemplary technique for measuring film thickness is based on Fast Fourier Transform (FFT) of reflective radiation obtained from a broad-band spectrometer, which is disclosed in U.S. patent application Ser. No. 09/920,341 entitled "Methods For High-Precision Gap Orientation Sensing Between a Transparent Template and Substrate For Imprint Lithography", which is incorporated by reference herein in its entirety. For multi-layer films, the technique may provide an average thickness of each thin film and its thickness variations by measuring at a predetermined number of sub-portions in one of processing regions a–l, e.g., 1,000 sub-portions. Employing FFT thickness measurement techniques, reflective radiation is digitized/quantized and a wave number obtained. The quantized data is then mapped into the frequency domain processing the same employing an FFT algorithm. In the frequency domain, one or more peaks, shown in FIG. 12 as $p_1$ and $p_2$, are obtained, one of which may correspond to the film thickness at one of the sub-portions of one of processing regions a–l. For a clearly defined single peak, for example, $p_1$, the film thickness (t) may be a function of the frequency around which peak $p_1$ is centered. This may be derived or determined from a priori information.

For example, after obtaining film thickness measurements at several or all of the sub-portions, a mean value is derived from these thickness measurements. Thereafter, each of the film thickness measurements are compared to the mean value. If any one of the thickness measurements vary from the mean more than a predetermined threshold it may be determined that an anomaly with respect to the film thickness measurement in associated processing region a–l is present. Furthermore, the location of the anomaly within the processing region may be ascertained. The actual value of the threshold may be any desired and is typically dependent upon several factors, such as the design tolerance of the pattern, the thickness of the film and the like. Alternatively, it has been found to determine anomalies as a variation from a standard deviation from the mean value. To that end, the standard deviation, either first, second, third standard deviation and the like, from the mean is compared with a predetermined threshold. From the foregoing the film thickness in each of the processing regions a–l may be determined, as well as whether a film thickness anomaly is present.

Figure 13:
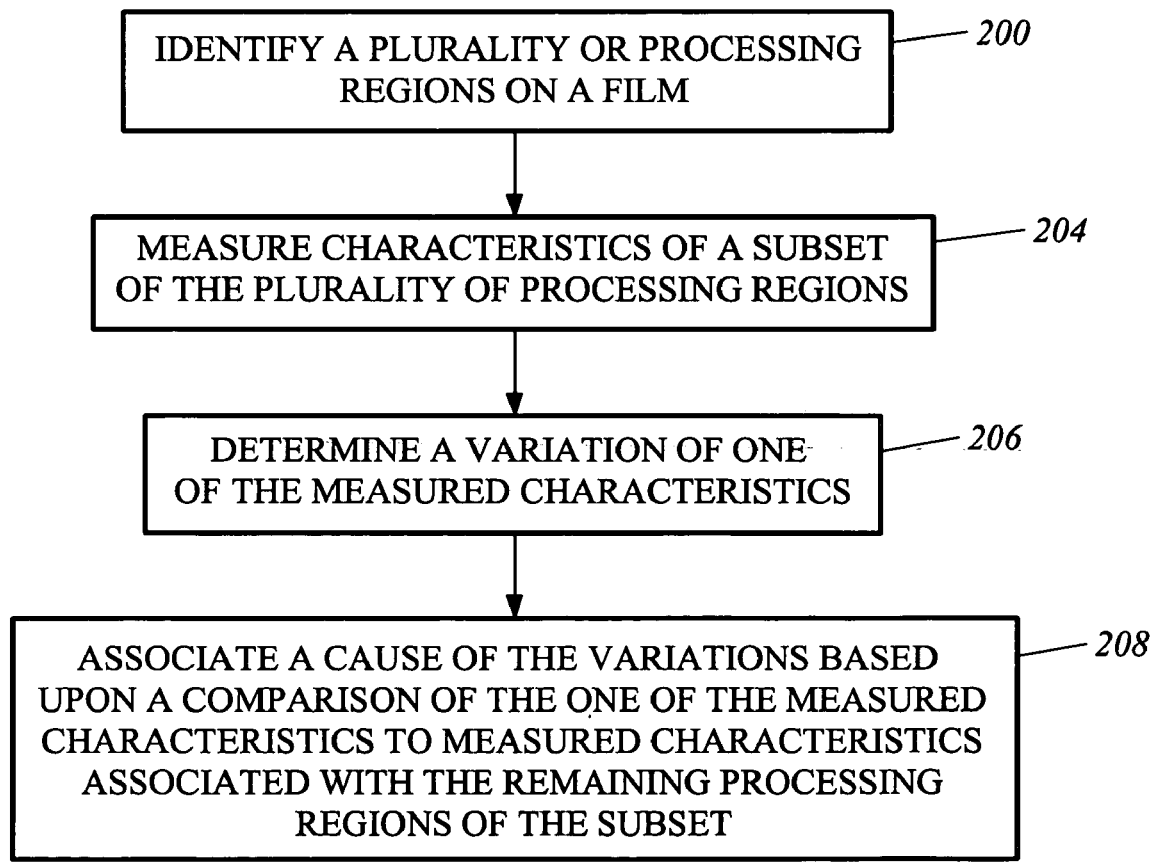
FIG. 13 is a flow chart showing a process for measuring characteristics of a film in accordance with the present invention.

Referring to FIGS. 1 and 13, in operation, a plurality of processing regions is identified at step 200. At step 202 the characteristics of a subset of the plurality of processing regions are measured. The subset may include all of the processing regions a–l. Determined, at step 204 are a variation of one or more of the measured characteristics, using one or more of the measurement techniques mentioned above. In the present example, assume an anomaly was found in processing region b. At step 206, a cause of the variation in processing region b is determined based upon a comparison with measured characteristics associated with processing regions a and c–l. To facilitate the aforementioned operation, processor 26 is coupled to a memory 106 that stores code to be operated on by processor 26. The code includes a first subroutine to control the sensing device 62, shown in FIG. 8, to impinge optical radiation on the plurality of processing regions a–l and detect optical radiation reflected therefrom. A second subroutine is included that controls the operations of the sensing device to obtain a predetermined number of measurements in the one of said plurality of processing regions a–l and quantizing the predetermined number of measurements to obtain a mean value, with the first subroutine determining the variation by comparing mean value with a predetermined threshold, which may be established as desired and/or based upon the application.

Figure 14:
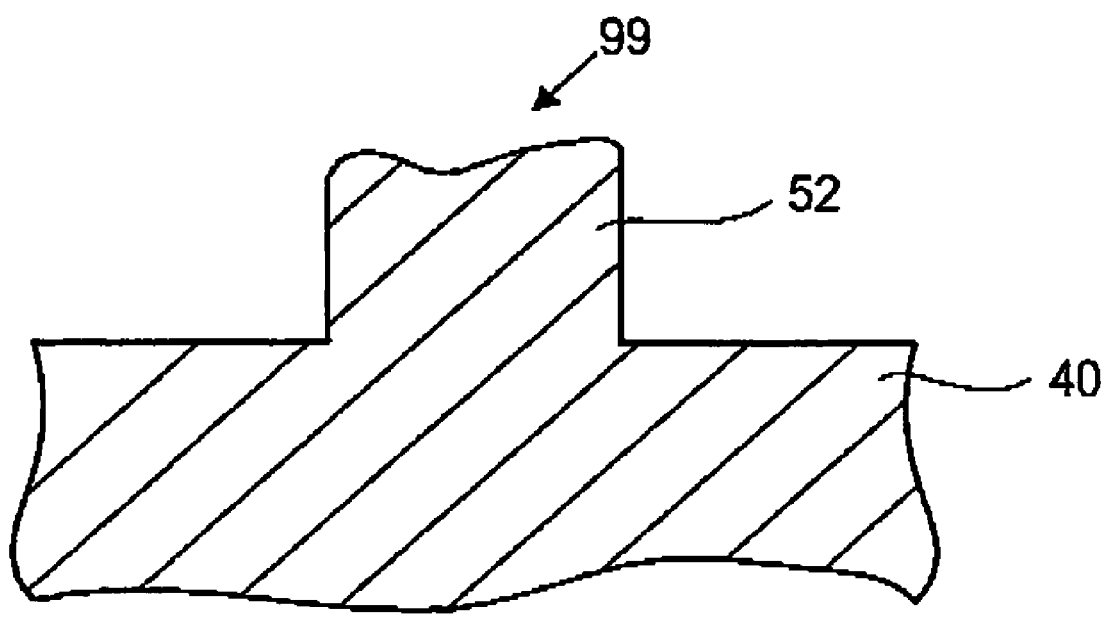
FIG. 14 is a side view of the imprinting layer shown in FIG. 5, having a defect therein.

The embodiments of the present invention described above are exemplary. Although the invention has been described with respect to measuring film thickness anomalies, other anomalies may be determined. For example, distortions 99 in the pattern may formed in imprinting layer 40, shown as a loss of planarity in sub-portion 52 in FIG. 14, may be sensed and the cause of the same determined employing the present invention. As a result, the system may be employed to detect anomalies in critical dimension variations of the pattern features, as well as, errors in field-to-field and/or layer-to-layer alignment. With such information adaptive control may be employed to correct/compensate for such anomalies. These measurements may be made either in-situ or post processes. Furthermore, the invention has been discussed with respect to being placed upon an imprint lithography machine. However, the invention may be performed by a separate machine and apart from the imprint lithography process.

As a result, many changes and modifications may be made to the disclosure recited above, while remaining within the scope of the invention. Therefore, the scope of the invention should not be limited by the above description, but instead should be determined with reference to the appended claims along with their full scope of equivalents.

What is claimed is:

1. A method for measuring characteristics of a film disposed on a substrate, said method comprising:
   identifying a plurality of processing regions on said film;
   measuring characteristics of a subset of said plurality of processing regions, defining measured characteristics;
   determining a variation of one of said measured characteristics; and
   associating a cause of said variation based upon a comparison of said one of said measured characteristics to measured characteristics associated with the remaining processing regions of said subset.

2. The method as recited in claim 1 wherein said variation is a defect.

3. The method as recited in claim 1 wherein said variation is an alignment error.

4. The method as recited in claim 1 wherein said variation is a critical dimension variation.

5. The method as recited in claim 1 wherein said cause is selected from a set of causes comprising a defect associated with an imprint head defining an imprint head defect, a defect associated with a support stack defining a support stack defect, a defect associated with a template defining a template defect and a defect associated with a substrate defining a substrate defect.

6. The method as recited in claim 1 wherein measuring further includes obtaining a predetermined number of measurements in one of said plurality of processing regions and quantizing said predetermined number of measurements and obtaining a mean value and, with determining said variation further including comparing said mean value with a predetermined threshold.

7. The method as recited in claim 1 wherein measuring further includes obtaining a predetermined number of measurements in one of said plurality of processing regions and quantizing said predetermined number of measurements and obtaining a mean value and a standard deviation from said mean value, with determining said variation further including comparing said standard deviation with a predetermined threshold.

8. The method as recited in claim 1 wherein associating further includes ascertaining an additional variation in remaining processing regions of said subset having features common to said variation and associating said cause with one of a detect associated with a template defining a template defect and a defect associated with an imprint head defining an imprint head defect.

9. The method as recited in claim 1 wherein associating further includes finding an absence of similarities between said variation and characteristics of the remaining processing regions of said subset and associating said cause with one of a defect associated with a support stack defining a support stack defect and defect associated with a substrate defining a substrate defect.

10. The method as recited in claim 1 wherein measuring further includes impinging optical radiation upon said plurality of processing regions and sensing optical radiation reflecting from said film containing information corresponding to said characteristics.

11. A method for measuring characteristics of a film disposed on a substrate, said method comprising:
   identifying a plurality of processing regions on said film;
   measuring characteristics of a subset of said plurality of processing regions, defining measured characteristics;
   obtaining a mean value and a standard deviation from said mean value for one of said measured characteristics;
   determining a variation of said one of said measured characteristics by comparing said standard deviation with a predetermined threshold; and
   associating a cause of said variation based upon a comparison of said one of said measured characteristics to measured characteristics associated with the remaining processing regions of said subset.

12. The method as recited in claim 11 wherein said cause is selected from a set of causes comprising a defect associated with an imprint head defining an imprint head defect, a defect associated with a support stack defining a support stack defect, a defect associated with a template defining a template defect and a defect associated with a substrate defining a substrate defect.

13. The method as recited in claim 11 wherein said cause is selected from a set of causes consisting of an alignment error and a critical dimension variation.

14. The method as recited in claim 12 wherein associating further includes ascertaining an additional variation in remaining processing regions of said subset having features common to said variation and associating said cause with one of said template defect and said imprint head defect.

15. The method as recited in claim 12 wherein associating further includes finding an absence of similarities between said variation and characteristics of the remaining processing regions of said subset and associating said cause with one of said substrate defect and said support stack detect.

16. A method for measuring characteristics of a film disposed on a substrate, said method comprising:
identifying a plurality of processing regions on said film;
measuring characteristics of a subset of said plurality of processing regions, defining measured characteristics;
determining an anomaly among said measured characteristics; and
associating a source of said anomaly based upon a comparison of said anomaly in said measured characteristics with characteristics in the remaining of said processing regions.

17. The method as recited in claim 16 wherein said source is selected from a set of causes comprising a defect associated with an imprint head defining an imprint head defect, a defect associated with a support stack defining a support stack defect, a defect associated with a template defining a template defect and a defect associated with a substrate defining a substrate defect.

18. The method as recited in claim 17 wherein measuring further includes obtaining a predetermined number of measurements in one of said plurality of processing regions and quantizing said predetermined number of measurements and obtaining a mean value and comparing said mean value with a predetermined threshold.

19. The method as recited in claim 17 wherein measuring further includes obtaining a predetermined number of measurements in one of said plurality of processing regions and quantizing said predetermined number of measurements and obtaining a mean value and a standard deviation from said mean value and comparing said standard deviation with a predetermined threshold.

20. The method as recited in claim 19 wherein associating further includes ascertaining an additional defect in the remaining processing regions of said subset having features common to said defect and associating said cause with one of said imprint head defect and said template defect.

21. The method as recited in claim 19 wherein associating further includes finding an absence of similarities between said defect and said additional defect in the remaining processing regions of said subset and associating said cause with one of said support stack defect and said substrate defect.

22. The method as recited in claim 19 wherein measuring further includes impinging optical radiation upon said plurality of processing regions and sensing optical radiation film containing information corresponding to said characteristics.

23. A system for measuring characteristics of a film disposed on a substrate, said system comprising:
a substrate support stack;
a substrate disposed on said substrate support stack;
an imprint head;
a template disposed on said imprint head;
a sensing system; and
a means for identifying a plurality of processing regions, a subset of which has characteristics associated therewith, and ascertaining a cause of an anomaly in characteristics of one of said plurality of processing regions by comparing of the characteristics of said one of said plurality of processing regions with characteristics associated with the remaining processing regions of said subset.

24. The system as recited in claim 23 further including a source of radiation to direct radiation along a path toward said support stack, with said template being disposed within said path and being transparent to said radiation.

25. The system as recited in claim 23 wherein said means for identifying further includes a processor and a memory device storing code to be operated on said processor, with said code including a first subroutine to control said sensing device to impinge optical radiation on the plurality of processing region of said subset and detect optical radiation reflected therefrom.

26. The system as recited in claim 25 wherein said cause is selected from a set of causes comprising a defect associated with an imprint head defining an imprint head defect, a defect associated with a support stack defining a support stack detect, a defect associated with a template defining a template defect and a defect associated with a substrate defining a substrate defect.

27. The system as recited in claim 25 said code further includes a second subroutine to control the operations of sad sensing device to obtain a predetermined number of measurements in said one of said plurality of processing regions and quantizing said predetermined number of measurements to obtain a mean value, with said first subroutine determining said variation by comparing said mean value with a predetermined threshold.

28. The system as recited in claim 25 said code further includes a second subroutine to control the operations of said sensing device to obtain a predetermined number of measurements in said one of said plurality of processing regions and quantizing said predetermined number of measurements to obtain a mean value and a standard deviation from said mean value, with said first subroutine determining said variation by comparing said standard deviation value with a predetermined threshold.

* * * * *